US012599659B2

(12) United States Patent
Sellers

(10) Patent No.: US 12,599,659 B2
(45) Date of Patent: Apr. 14, 2026

(54) ATTENUATED AVIAN REOVIRUS STRAINS 94826 C140 AND 96139 C140

(71) Applicant: UNIVERSITY OF GEORGIA RESEARCH FOUNDATION, INC., Athens, GA (US)

(72) Inventor: Holly S. Sellers, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 926 days.

(21) Appl. No.: 17/779,811

(22) PCT Filed: Dec. 1, 2020

(86) PCT No.: PCT/US2020/062651
§ 371 (c)(1),
(2) Date: May 25, 2022

(87) PCT Pub. No.: WO2021/113206
PCT Pub. Date: Jun. 10, 2021

(65) Prior Publication Data
US 2023/0000972 A1 Jan. 5, 2023

Related U.S. Application Data

(60) Provisional application No. 62/942,426, filed on Dec. 2, 2019.

(51) Int. Cl.
| | |
|---|---|
| *A61K 39/15* | (2006.01) |
| *A61K 39/12* | (2006.01) |
| *A61P 31/14* | (2006.01) |
| *C07K 16/10* | (2006.01) |
| *C12N 7/00* | (2006.01) |
| *A61K 39/00* | (2006.01) |

(52) U.S. Cl.
CPC .............. *A61K 39/12* (2013.01); *A61K 39/15* (2013.01); *A61P 31/14* (2018.01); *C07K 16/10* (2013.01); *C12N 7/00* (2013.01); *A61K 2039/5254* (2013.01); *C12N 2720/12021* (2013.01); *C12N 2720/12034* (2013.01); *C12N 2720/12064* (2013.01)

(58) Field of Classification Search
None
See application file for complete search history.

(56) References Cited

U.S. PATENT DOCUMENTS

| | | | |
|---|---|---|---|
| 6,951,650 | B1 | 10/2005 | Van Loon |
| 9,968,671 | B2 | 5/2018 | Sellers |
| 10,588,958 | B2 | 3/2020 | Sellers |
| 11,090,377 | B2 | 8/2021 | Sellers |
| 2010/0055131 | A1 | 3/2010 | Sellers |
| 2016/0256554 | A1 | 9/2016 | Genin |
| 2017/0028055 | A1 | 2/2017 | Sellers |
| 2018/0236061 | A1 | 8/2018 | Sellers |
| 2023/0000972 | A1* | 1/2023 | Sellers ................... A61P 31/14 |

FOREIGN PATENT DOCUMENTS

| | | | | |
|---|---|---|---|---|
| EP | 4069289 | A1 | 10/2022 | |
| UA | 90976 | C2 | 6/2010 | |
| WO | WO-9924582 | A1 | 5/1999 | |
| WO | WO-2009093251 | A2 | 7/2009 | |
| WO | WO-2009093251 | A3 | 10/2009 | |
| WO | WO-2015116778 | A1 * | 8/2015 | .............. A61P 43/00 |
| WO | WO-2017210262 | A1 | 12/2017 | |

OTHER PUBLICATIONS

Bampi RA. (Pathogenicity of variant field isolates of avian reovirus and molecular characterization of Brazilian variants from commercial broilers (Doctoral dissertation, University of Georgia, 2016).*
Alvarado I., et al., "Evaluation of Progeny Protection Against a Novel Reovirus Strain Associated with Lameness and Poor Performance", International Poultry Scientific Forum, Abstract No. T97, Georgia World Congress Center, Atlanta, Georgia, Jan. 27-28, 2014, Available online [Retrieved on May 24, 2015], Retrieved from the Internet:ippexpo.org/ipsf/docs/2014%20IPSF%20Abstracts.pdf], 3 pages.
Alvarado I.R, "Reovirus Outbreaks in Broilers and Broiler Breeders", 2013 [Retrieved from the Internet May 20, 2015, thepoultryfederation.com/public/userfiles/files/Reovirus%20in%20Broilers%20%20Broiler%20Breeders.pdf] 35 pages.
"Big Encyclopedic Dictionary", published on Nov. 22, 2007, according to the Wayback Machine, https://dic.academic.ru/dic.nsf/enc3p/206970), 1 page.
Calvo P.G., et al., "Structure of the Carboxy-Terminal Receptor-Binding Domain of Avian Reovirus Fibre Sigma C," Journal of Molecular Biology, Nov. 18, 2005, vol. 354, No. 1, pp. 137-149. Epub Sep. 30, 2005.
Drastini Y., et al., "Chymotrypsin and Trypsin Sensitivities of Avian Reoviruses", Canadian Journal of Veterinary Research, 1994, vol. 58, pp. 75-78.
Goldenberg D., et al., "Genetic and Antigenic Characterization of Sigma C Protein from Avian Reovirus", Avian Pathology, Jun. 11, 2010, vol. 39, No. 3, pp. 189-199.
"Innovations in Poultry Vaccines—Effervescent Table Advances Delivery", International Poultry Production, vol. 23, No. 7, 2015, p. 35, 2 Pages.

(Continued)

*Primary Examiner* — Shanon A. Foley
(74) *Attorney, Agent, or Firm* — Mueting Raasch Group

(57) ABSTRACT

Attenuated isolates of avian reoviruses associated viral arthritis/tenosynovitis in poultry are presented, including avian reovirus strain 94826 C140 deposited at the ATCC under Patent Designation PTA-126077 and progeny or derivatives thereof and avian reovirus strain 96139 C140 deposited at the ATCC under Patent Designation PTA-126078 and progeny or derivatives thereof. Compositions and methods for administering the isolates or compositions as vaccines to control of reovims-induced viral arthritis/tenosynovitis in birds of the order Galliformes are also presented.

26 Claims, No Drawings

(56)                 References Cited

OTHER PUBLICATIONS

International Preliminary Report on Patentability for International Application No. PCT/US2020/062651, mailed Jun. 16, 2022, 8 Pages.

International Search Report and Written Opinion for International Application No. PCT/US2020/062651, mailed Apr. 7, 2021, 11 Pages.

Kant A., et al., "Classification of Dutch and German Avian Reoviruses by Sequencing the sigma C protein," Veterinary Research, Mar.-Apr. 2003, vol. 34, No. 2, pp. 203-212.

Kool D.A., et al., "UniProtKB/TrEMBL Submission Q84144 9REOV", The S1 Gene Sequences of Two Australian Avian Reoviruses, Aug. 10, 2010, Retrieved from the Internet May 22, 2015, uniprot.org/uniprot/Q84144.txt?version=23] 1 page.

Li S.K., et al., "Development of a Reliable Assay Protocol for Identification of Diseases (RAPID)—Bioactive Amplification with Probing for Detection of Avian Reovirus," Journal of Virological Methods, Apr. 2008, vol. 149, No. 1, pp. 35-41, Epub Mar. 4, 2008.

Liu H.J., et al., "Molecular Evolution of Avian Reovirus: Evidence for Genetic Diversity and Reassortment of the S-class Genome Segments and Multiple Cocirculating Lineages", Virology, Sep. 15, 2003, vol. 314, No. 1, pp. 336-349.

Liu H.J., et al., "Rapid Characterization of Avian Reoviruses using Phylogenetic Analysis, Reverse Transcription-Polymerase Chain Reaction and Restriction Enzyme Fragment Length Polymorphism", Avian Pathology, Apr. 2004, vol. 33, No. 2, pp. 171-180.

"Merial Launches Effervescent Tablet Vaccine for Newcastle Disease", Sep. 9, 2015, 2 Pages.

Sellers H.S., "Isolation and Characterization of Novel Avian Reoviruses in Commercial Broilers from Clinical Cases of Tenosynovitis" Department of Population Health Poultry Diagnostic & Research center, College of Veterinary Medicine, University of Georgia, Feb. 7, 2013, 5 pages. Presented at Georgia World Congress Center, Atlanta, Georgia, Jan. 27-28, 2014, 5 Pages.

Shmulevitz., et al., "Sequential Partially Overlapping Gene Arrangement in the Tricistronic S1 Genome Segments of Avian Reovirus and Nelson Bay Reovirus: Implications for Translation Initiation", Journal of Virology, Jan. 2002, vol. 76, No. 2, pp. 609-618.

Tarantul V.Z., et al., "The Dictionary of Biotechnological Terms Edited by Doctor of Biological Sciences", Moscow, 2005, 2 Pages, p. 104.

"Tenosynovitis Vaccine", 9 CFR Ch. I (Jan. 1, 2011 Edition) 2011, pp. 786-788.

Van Der Heide L., et al., "Development of an Attenuated Apathogenic Reovirus Vaccine Against Viral Arthritis/Tenosynovitis", American Association of Avian Pathologists, Avian Diseases, Sep. 1, 1983, vol. 27, No. 3, pp. 698-706, ISSN: 0005-2086, XP002915466, abstract, tables 1-5.

* cited by examiner

ATTENUATED AVIAN REOVIRUS STRAINS 94826 C140 AND 96139 C140

CONTINUING APPLICATION DATA

This application is a $371 National Stage application of PCT/US2020/062651 with an international filing date of Dec. 1, 2020, which claims the benefit of U.S. Provisional Application Ser. No. 62/942,426, filed Dec. 2, 2019, both of which are incorporated by reference herein.

BACKGROUND

Avian reoviruses are associated with several diseases in poultry, including malabsorption syndrome and runting and stunting syndrome (RSS), although their role as primary pathogens in these clinical syndromes is not clear. In contrast, the association of avian reoviruses with clinical cases of viral arthritis/tenosynovitis is quite clear, as reoviruses have been isolated from the tendons of affected birds. The control of reovirus-induced viral arthritis/tenosynovitis can be achieved by vaccination of broiler breeders with a combination of live and/or inactivated vaccines with maternal immunity passed on to progeny for early protection against field challenge. In broilers, live attenuated vaccines are available for use at day-of-hatch and for use in ovo. Current commercial vaccine strains (S1133, 1733, 2408, and 2177 to name a few) were isolated in the 1960-1970s and do not provide protection against currently circulating reovirus isolates from confirmed cases of viral arthritis/tenosynovitis. Thus, there is a need for the isolation and characterization of currently circulating avian reoviruses and the development of effective vaccines.

SUMMARY OF THE INVENTION

The present invention includes an isolated avian reovirus, wherein the isolated avian reovirus is the avian reovirus strain 94826 C140 deposited at the ATCC under Patent Designation PTA-126077, or a progeny or derivative thereof, wherein a progeny or derivative thereof has essentially the same biological and serological characteristics of the avian reovirus strain 94826 C140 deposited at the ATCC under Patent Designation PTA-126077.

The present invention includes an isolated avian reovirus, wherein the isolated avian reovirus is the avian reovirus strain 96139 C140 deposited at the ATCC under Patent Designation PTA-126078, or a progeny or derivative thereof, wherein a progeny or derivative thereof has essentially the same biological and serological characteristics of the avian reovirus strain 96139 C140 deposited at the ATCC under Patent Designation PTA-126078.

In some aspects, the present invention includes a Master Seed virus preparation of an avian reovirus as described herein.

In some aspects, the isolated avian reovirus is lyophilized, freeze dried, frozen, or an effervescent tablet.

In some embodiments, the present invention includes a composition including an isolated avian reovirus as described herein. In some aspects, a composition includes an adjuvant. In some aspects, a composition includes a pharmaceutically acceptable carrier. In some aspects, the composition is formulated for intranasal, intraocular, oral, mucosal, intramuscular, subcutaneous, or in ovo administration. In some aspects, the composition is formulated for spraying or aerolizing.

In some embodiments, the present invention includes a vaccine including an isolated avian reovirus as described herein or a composition as described herein. In some aspects, the vaccine reduces the susceptibility of a bird of the order Galliformes to reovirus-induced viral arthritis/tenosynovitis. In some aspects, the reovirus-induced viral arthritis/tenosynovitis is a variant group 1/genotype 5-induced viral arthritis/tenosynovitis. In some aspects, the reovirus-induced viral arthritis/tenosynovitis is a variant group 2/genotype 1-induced viral arthritis/tenosynovitis.

In some embodiments, the present invention includes a vaccine for birds of the order Galliformes comprising an amount of the avian reovirus strain 94826 C140 deposited at the ATCC under Patent Designation PTA-126077, or a progeny or derivative thereof, sufficient to protect the birds from reovirus-induced viral arthritis/tenosynovitis, and a pharmaceutically acceptable carrier. In some aspects, the reovirus-induced viral arthritis/tenosynovitis is a variant group 1/genotype 5-induced viral arthritis/tenosynovitis.

In some embodiments, the present invention includes a vaccine for birds of the order Galliformes comprising an amount of the avian reovirus strain avian reovirus strain 96139 C140 deposited at the ATCC under Patent Designation PTA-126078, or a progeny or derivative thereof, sufficient to protect the birds from reovirus-induced viral arthritis/tenosynovitis, and a pharmaceutically acceptable carrier. In some aspects, the reovirus-induced viral arthritis/tenosynovitis is a variant group 2/genotype 1-induced viral arthritis/tenosynovitis.

In some embodiments, the present invention includes an effervescent tablet comprising an avian reovirus, composition, or vaccine as described herein.

The present invention includes a method for reducing susceptibility of a bird of the order Galliformes against reovirus-induced viral arthritis/tenosynovitis, the method comprising administering to the bird an avian reovirus, composition, or vaccine as described herein.

The present invention includes a method for protecting a bird of the order Galliformes against reovirus-induced viral arthritis/tenosynovitis, the method comprising administering to the bird an avian reovirus, composition, or vaccine as described herein.

In some aspects of the methods described herein, the reovirus-induced viral arthritis/tenosynovitis is a variant group 1/genotype 5-induced viral arthritis/tenosynovitis. In some aspects, the reovirus-induced viral arthritis/tenosynovitis is a variant group 2/genotype 1-induced viral arthritis/tenosynovitis. In some aspects, of the methods described herein, administration is intranasal, intraocular, oral, mucosal, intramuscular, or subcutaneous. In some aspects, of the methods described herein, administration includes in ovo administration. In some aspects, of the methods described herein, the avian reovirus, composition, or vaccine is administered by aerosol. In some aspects, of the methods described herein, the avian reovirus, composition, or vaccine is administered by drinking water. In some aspects, the bird is a chicken or turkey. In some aspects, of the methods described herein, administration is to a breeder hen or a rooster.

The present invention includes a of producing anti-reovirus antibodies in poultry, the method comprising administering an isolated avian reovirus, composition, or vaccine as described herein to the bird. In some aspects, the bird is a chicken or turkey.

The present invention includes a diagnostic kit including an isolated avian reovirus as described herein.

The present invention includes a method of detecting exposure to an avian reovirus in a bird, the method comprising determining that an antisera sample obtained from the bird specifically binds to an avian reovirus as described herein. In some aspects, the bird is a chicken or turkey.

The present invention includes a hyperimmune sera to an avian reovirus as described herein.

The present invention includes an antibody that binds to an avian reovirus as described herein and does not bind to avian reovirus strain S1133, 1733, 2408, and/or 2177. In some aspects, the antibody is a monoclonal antibody.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

The present invention provides two attenuated avian reovirus strains, avian reovirus strain 94826 C140 and avian reovirus strain 96139 C140, and progeny, and derivatives thereof. These attenuated reovirus strains are safe and efficacious when administered to birds as live formulations in preventing avian reovirus infections and reducing the incidence and severity of reovirus-induced viral arthritis and/or tenosynovitis.

In one aspect, the present invention includes avian reovirus strain 94826 C140 and progeny and derivatives thereof. Avian reovirus strain 94826 C140 is an attenuation of the avian reovirus strain 94826, obtained by passaging the avian reovirus strain 94826 one hundred forty times in chicken embryos. Avian reovirus strain 94816 is a Group 1/Genotype 5 reovirus associated with viral arthritis and tenosynovitis in poultry. Avian reovirus strain 94816 is described in more detail in International Application No. PCT/US2015/013449 (WO 2015/116778) and U.S. patent application Ser. No. 15/223,623, which are hereby incorporated by reference in their entireties. Attenuated avian reovirus strain 94826 C140 is also a Group 1/Genotype 5 avian reovirus. Attenuated avian reovirus strain 94826 C140 was deposited with the American Type Culture Collection (ATCC®), 10801 University Boulevard, Manassas, VA 20110-2209, USA, under Patent Deposit Designation as PTA-126077 on Aug. 13, 2019. This deposit was in accordance with the Budapest Treaty on the International Recognition of the Deposit of Microorganisms for the Purposes of Patent Procedure. Attenuated avian reovirus 94826 C140 is also archived as PDRC ref: 121116 in the virus repository at the Poultry Diagnostic and Research Center (PDRC) at the University of Georgia, located at 953 College Station Road Athens Georgia, 20602. The safety and efficacy of avian reovirus strain 94826 C140 as a live, attenuated reovirus vaccine is described in more detail in Example 3.

In another aspect, the present invention includes avian reovirus strain 96139 C140 and progeny and derivatives thereof. Avian reovirus strain 96139 C140 is an attenuation of avian reovirus strain 96139, obtained by passaging the avian reovirus strain 96139 one hundred forty times in chicken embryos. Avian reovirus strain 96139 is a Group 2/Genotype 1 avian reovirus associated with viral arthritis and tenosynovitis in poultry. Avian reovirus strain 96139 is described in more detail in International Application No.

PCT/US2015/013449 (WO 2015/116778) and U.S. patent application Ser. No. 15/223,623, which are hereby incorporated by reference in their entireties. Avian reovirus strain 96139 was deposited with the ATCC® under Patent Deposit Designation as PTA-125688 on Mar. 7, 2019. Attenuated avian reovirus 96139 C140 is also a Group 2/Genotype 1 avian reovirus. Attenuated avian reovirus 96139 C140 was deposited with the American Type Culture Collection) (ATCC®, 10801 University Boulevard, Manassas, VA 20110-2209, USA, under Patent Deposit Designation as PTA-126078 on Aug. 13, 2019. This deposit was in accordance with the Budapest Treaty on the International Recognition of the Deposit of Microorganisms for the Purposes of Patent Procedure. Attenuated avian reovirus 9619 C140 is also archived as PDRC ref: 119812 in the virus repository at the Poultry Diagnostic and Research Center (PDRC) at the University of Georgia, located at 953 College Station Road Athens Georgia, 20602. The safety and efficacy of avian reovirus strain 96139 C140 as a live, attenuated reovirus vaccine is described in more detail in Example 3.

As discussed in more detail in International Application No. PCT/US2015/013449 (WO 2015/116778) and U.S. patent application Ser. No. 15/223,623, avian reovirus strains 94826 and 96139 represent two genetically and serologically distinct groups of avian reoviruses that have been isolated from clinical cases of tenosynovitis. Genetic analysis of their avian reovirus sigma C proteins reveals novel genotypes unrelated to current avian reovirus vaccine strains.

Avian reoviruses, along with mammalian reoviruses, comprise the genus Orthoreovirus in the family Reoviridae. These viruses contain 10 dsRNA genome segments enclosed within a non-enveloped, icosahedral double capsid of approximately 80 nm. The genome segments can be separated based on electrophoretic mobility into three large (L1, L2, L3), three medium (M1, M2, M3) and four small (S1, S2, S3, S4) segments which code for proteins $\lambda 1$, $\lambda 2$, $\lambda 3$, $\mu 1$, $\mu 2$, $\mu NS$, $\sigma 3$, $\sigma 1$, $\sigma 2$, $\sigma NS$, respectively. The $\sigma 2$ protein is an outer capsid protein which carries group-specific neutralizing epitopes. It also binds double-stranded RNA and has been identified as a zinc metalloprotein. The sigma C protein, the minor outer capsid protein encoded by the $\sigma 1$ segment, is the target for molecular characterization of avian reoviruses and is responsible for cell attachment, as well as induction of type-specific neutralizing antibodies. An avian reovirus virion includes a capsid, a core, and a nucleoprotein complex. The virus capsid is not enveloped. The capsid/nucleocapsid is isometric with icosahedral symmetry and has a diameter of about 80-82 nm. The capsid shells of virions are composed of two layers. All shells are usually present, or the outer shell is often lost during preparation. Capsids appear round. The capsid surface structure reveals a regular pattern with distinctive features. The capsomer arrangement is clearly visible. Surface projections are not present. Inner capsids core has a diameter of about 60 nm. Virus preparations contain one particle component. The core is spherical and consists of the dsRNA genome with a diameter of about 49 nm. The ends of the fibers protrude almost through to the capsid surface.

The present invention includes Master Seed virus preparations prepared from avian reovirus strain 94826 C140 (deposited with the ATCC® under Patent Deposit Designation as PTA-126077 on Aug. 13, 2019) or avian reovirus strain 96139 C140 (deposited with the ATCC® under Patent Deposit Designation as PTA-126078 on Aug. 13, 2019). Master Seed virus preparation of the present invention may be prepared and tested according to Title 9 of the Code of Federal Regulations (CFR) § 113.332 (Tenosynovitis Vaccine).

Also included in the present invention are isolated progeny and isolated derivatives of avian reovirus strain 94826 C140 (deposited with the ATCC® under Patent Deposit Designation as PTA-126077 on Aug. 13, 2019) and avian reovirus strain 96139 C140 (deposited with the ATCC® under Patent Deposit Designation as PTA-126078 on Aug. 13, 2019) with equivalent or similar biological, serological, and/or genetic characteristics. As used herein, serological, biological, and genetic characteristics may include one or more of the characteristics described in the data in the Examples included herewith. More particularly, progeny or derivative strains of PTA-126077 or PTA-1260789495 may retain the particularly favorable protective properties belonging to the present invention, as described in more detail in the examples included herewith.

Avian reovirus according to the invention can be propagated by conventional methods, including, but not limited to, any of those described in the examples section included herewith. In brief, a substrate able to support the replication of an avian reovirus is inoculated with an avian reovirus of the present invention and propagated until the virus is replicated to a desired infectious titer, or antigen mass content. Reovirus containing material is then harvested. Suitable substrates may include embryonated eggs, primary (avian) cell cultures, such as, for example, chicken embryo liver cells, chicken embryo fibroblasts, or chicken kidney cells, mammalian cell lines, such as, for example, the VERO cell line or the BGM-70 cell line, or avian cell lines, such as, for example, QT-35, QM-7 or LMH.

The present invention includes compositions and vaccines including one or more of the isolated viruses described herein. Vaccine preparations of the present invention may be prepared and tested according to Title 9 of the Code of Federal Regulations (CFR) § 113.332 (Tenosynovitis Vaccine).

In some embodiments, the virus is live. In some embodiments, the virus is inactivated or killed. In some embodiments, a virus or composition or vaccine thereof may be lyophilized. In some embodiments, a virus or composition or vaccine thereof may be frozen. In some embodiments, a virus or composition or vaccine thereof may be freeze dried.

In some embodiments, a virus or composition or vaccine thereof may be formulated as an effervescent table. Such effervescent tablets may, for example, be packaged in lightweight aluminum blisters. The table may be dissolved in water and administered, for example, orally, nasally, or by aerosol spray, whereby droplets enter via the mucus membranes of the birds.

Such a compositions and vaccine may be administered as the active component to immunize a bird to elicit an immune response to a group 1 and/or group 2 avian reovirus and/or induce immunity against such an avian reovirus. Immunity may include the induction of a higher level of protection in a population of birds after vaccination compared to an unvaccinated group. The immune response may, or may not, confer protective immunity. An immune response may, for example, include one or more of a cell mediated immune response, which involves the production of lymphocytes in response to exposure to the antigen and/or a humoral immune response, which involves production of plasma lymphocytes (B cells) in response to antigen exposure with subsequent antibody production. Immunization may result in the reduction, inhibition, or prevention of one or more of the symptoms of avian reovirus associated viral arthritis (VA)/tenosynovitis. Such symptoms may include one or more of body weight suppression, decrease in egg production, mortality, macroscopic lesions (including, but not limited to tendon swelling, tenosynovitis, tendon rupture, and hydropericardium), and histological changes (including, but not limited to lymphocytic tenosynovitis, lymphocytic epicarditis, and lymphocytic myocarditis).

A composition or vaccine of the present invention may also include one or more compounds with adjuvant activity. Suitable compounds or compositions for this purpose include aluminum hydroxide, aluminum phosphate, aluminum oxide, plant oils, animal oils, oil-in-water or water-in-oil emulsion based on, for example a mineral oil, such as Bayol F™ or Marcol 52™, Complete Freund's adjuvant, incomplete Freund's adjuvant, or a vegetable oil such as vitamin E acetate, and saponins.

A composition or vaccine of the present invention may include one or more suitable pharmaceutically acceptable carriers or diluents. An immunogenic composition or vaccine of the present invention may also contain one or more stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

A composition or vaccine of the present invention may further include one or more immunogens derived from other pathogens infectious to poultry. Such immunogens may be derived from, for example, Marek's disease virus (MDV), infectious bronchitis virus (IBV), Newcastle disease virus (NDV), egg drop syndrome (EDS) virus, turkey rhinotracheitis virus (TRTV), poxvirus, reovirus, chicken parvovirus, and avian nephritis virus (including, but not limited to ANV-1 and ANV-2).

A composition or vaccine of the present invention may be administered by any suitable known method of inoculating poultry including nasally, ophthalmically, by injection, in drinking water, in the feed, by exposure, in ovo, maternally, by respiratory inhalation, and the like. The immunogenic composition or vaccine may be administered by mass administration techniques such as by placing the vaccine in drinking water or by spraying or aerolizing. When administered by injection, the immunogenic composition or vaccine may be administered parenterally. Parenteral administration includes, for example, administration by intravenous, subcutaneous, intramuscular, or intraperitoneal injection.

In some embodiments, a live vaccine may be administered in a dose of not less than $10^2$ titration units (wherein titration units are defined in Title 9, Section 113.332, Code of Federal Regulations) per bird, and a vaccine may contain the antigenic equivalent of $10^4$-$10^{10}$ $TCID_{50}$ per bird (wherein TCID is an abbreviation for Tissue Culture Infective Dose).

In some embodiments, a live vaccine may be administered in a dose of about $10^{1.5}$ to about $10^7$ TCID or EID (embryo infective does).

In some aspects, a vaccine may contain the antigenic equivalent of about $10^{1.5}$ $TCID_{50}$ per bird, about $10^2$ $TCID_{50}$ per bird, about $10^3$ $TCID_{50}$ per bird, about $10^4$ $TCID_{50}$ per bird, about $10^5$ $TCID_{50}$ per bird, about $10^6$ $TCID_{50}$ per bird, about $10^7$ $TCID_{50}$ per bird, about $10^8$ $TCID_{50}$ per bird, about $10^9$ $TCID_{50}$ per bird, about $10^{10}$ $TCID_{50}$ per bird, or any range thereof.

Compositions and vaccines of the present invention may be substantially pure. As used herein, "substantially pure"

will mean material essentially free of any similar macro-molecules or other biological entities that would normally be found with it in nature.

Compositions and vaccines of the present invention may be administered to birds of any of a variety of avian species that are susceptible to infection with an avian reovirus, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. Chickens include, but are not limited to, hens, roosters, broilers, roasters, layers, breeders, the offspring of breeder hens, and layers. As used herein, the term "susceptible to" means the possibility or actuality of a detrimental response to the referenced microorganism, when compared to a non-susceptible individuals or groups, and/or one or more pathological state(s) indicative of avian reovirus infection.

The vaccine of the present invention may be administered to poultry before or after hatching. Poultry may receive a vaccine at a variety of ages. For example, broilers may be vaccinated in ovo, at one-day-old, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Also, in some embodiments, such laying stock or reproduction stock may be vaccinated within about the first two weeks of age. Such laying stock or reproduction stock may be boosted at about 16, at about 17, at about 18, at about 19, or at about 20 weeks of age. The offspring of such laying stock or reproduction stock may demonstrate an antibody titer to a polypeptide as described herein, which may prevent or mitigate the symptoms of an avian reovirus infection in the offspring. In ovo vaccination may take place, for example, at about 13 days, about 14 days, about 15 days, about 16 days, about 17 days, about 18 days, about 19 days, about 20 days, or at any range thereof.

Chickens may be vaccinated at any suitable age and are usually about one to three days old before first vaccination. The chickens may be vaccinated only once. Or, if two doses of vaccine are used, the first is given, for example, when the chickens are 3 days to a week old and subsequently after a further 1-10 weeks.

Multiple doses of the composition can be administered throughout the life of the chicken. As maternal immunity is a primary source of providing protection to broiler progeny, breeder chickens are typically vaccinated, although broiler chickens can be vaccinated if so desired.

The present invention includes a method of producing an anti-variant group 1 and/or variant group 2 avian reovirus immune response in poultry, the method including administering an isolated virus, composition or vaccine as described herein. In some aspects, immunity includes humoral and/or cellular immunity. In some aspects, immunity includes mucosal immunity.

The present invention includes a method of preventing an avian reovirus infection in poultry, the method including administering an isolated virus, composition or vaccine as described herein.

In some aspects of the methods of the present invention, administration includes injection, spraying, oral administration, or respiratory administration. In some aspects of the methods of the present invention, administration induces mucosal immunity. In some aspects of the methods of the present invention, administration includes in ovo administration. In some aspects, in ovo administration includes administration at about 13 days, about 14 days, about 15 days, about 16 days, about 17 days, about 18 days, about 19 days, about 20 days, or any range thereof.

The present invention includes a method of detecting exposure to a variant group 1 and/or a variant group 2 avian reovirus in a bird, the method including a determination of whether or not an antisera sample obtained from the bird specifically binds to a virus of the present invention. For example, the present invention includes the use of one or more avian reoviruses of the present invention in methods of detecting exposure to an avian reovirus in a bird, the method including determining that an antisera sample obtained from the bird specifically binds to an avian reovirus of the present invention.

The present invention also includes kits including one or more of the avian reoviruses of the present invention. The kit may include one or more containers filled with an avian reovirus of the present invention. In some aspects, the virus may be, for example, lyophilized, freeze dried, frozen, or formulated as an effervescent tablet. The kit may include additional, separate containers of other strains of avian reoviruses or other pathogens of poultry. Such a kit may include additional components, such as for example, a positive control virus, a negative control virus, a secondary antibody, and/or a detectable marker. Additionally, the kit may include other reagents such as buffers and solutions needed to practice the invention are also included. Optionally associated with such container(s) can be a notice or printed instructions. A kit of the present invention may include "packaging material." As used herein, the term "packaging material" refers to one or more physical structures used to house the contents of the kit. Packaging material is constructed by well known methods, preferably to provide a sterile, contaminant-free environment. Packaging material may be a solid matrix or a material such as glass, plastic, paper, foil, and the like.

The present invention provides methods for detecting and/or measuring the amount of a group 1 or group 2 avian reovirus in a sample obtained from a bird. Such a method may include contacting a sample with an antibody that selectively binds to an avian reovirus as described herein as described herein and measuring the amount of binding of the antibody to a virus or protein in the sample. The sample may be any biological material, such as tissue, bone, blood, urine or faeces. The methods of this aspect of the invention are useful, for example, for determining whether poultry are infected with an avian reovirus of the present invention. Infected animals so identified can then be isolated or killed in order to prevent spread of the reovirus to other animals.

As used herein, "isolated" refers to material removed from its original environment (e.g., the natural environment if it is naturally occurring), and thus is altered "by the hand of man" from its natural state.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also, herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

In several places throughout the application, guidance is provided through lists of examples, which examples can be used in various combinations. In each instance, the recited list serves only as a representative group and should not be interpreted as an exclusive list. It is to be understood that the particular examples, materials, amounts, and procedures are to be interpreted broadly in accordance with the scope and spirit of the invention as set forth herein.

All headings are for the convenience of the reader and should not be used to limit the meaning of the text that follows the heading, unless so specified.

The invention is defined in the claims. However, below is provided a non-exhaustive list of non-limiting embodiments. Any one or more of the features of these embodiments may be combined with any one or more features of another example, embodiment, or aspect described herein.

1. An isolated avian reovirus, wherein the isolated avian reovirus is the avian reovirus strain 94826 C140 deposited at the ATCC under Patent Designation PTA-126077, or a progeny or derivative thereof, wherein a progeny or derivative thereof has essentially the same biological and serological characteristics of the avian reovirus strain 94826 C140 deposited at the ATCC under Patent Designation PTA-126077.

2. An isolated avian reovirus, wherein the isolated avian reovirus is the avian reovirus strain 96139 C140 deposited at the ATCC under Patent Designation PTA-126078, or a progeny or derivative thereof, wherein a progeny or derivative thereof has essentially the same biological and serological characteristics of the avian reovirus strain 96139 C140 deposited at the ATCC under Patent Designation PTA-126078.

3. The isolated avian reovirus of embodiment 1 or 2, wherein the isolated avian reovirus comprises a Master Seed virus.

4. The isolated avian reovirus of any one of embodiments 1 to 3, wherein the isolated avian reovirus is lyophilized, freeze dried, frozen, or an effervescent tablet.

5. A composition comprising the isolated avian reovirus of any one of embodiments 1 to 4.

6. The composition of embodiment 5 comprising an adjuvant.

7. The composition of embodiment 5 or 6 comprising a pharmaceutically acceptable carrier.

8. The composition of any one of embodiments 5 to 7, wherein the composition is formulated for intranasal, intraocular, oral, mucosal, intramuscular, subcutaneous, or in ovo administration.

9. The composition of any one of embodiments 5 to 8, wherein the composition is formulated for spraying or aerolizing.

10. A vaccine comprising the isolated avian reovirus of any one of embodiments 1 to 4 or the composition of any one of embodiments 5 to 9.

11. The vaccine of embodiment 10, wherein the vaccine reduces the susceptibility of a bird of the order Galliformes to reovirus-induced viral arthritis/tenosynovitis.

12. A vaccine for birds of the order Galliformes comprising an amount of the avian reovirus strain 94826 C140 deposited at the ATCC under Patent Designation PTA-126077, or a progeny or derivative thereof, sufficient to protect the birds from reovirus-induced viral arthritis/tenosynovitis, and a pharmaceutically acceptable carrier.

13. The vaccine of embodiment 11 or 12, wherein the reovirus-induced viral arthritis/tenosynovitis is a variant group 1/genotype 5-induced viral arthritis/tenosynovitis.

14. A vaccine for birds of the order Galliformes comprising an amount of the avian reovirus strain avian reovirus strain 96139 C140 deposited at the ATCC under Patent Designation PTA-126078, or a progeny or derivative thereof, sufficient to protect the birds from reovirus-induced viral arthritis/tenosynovitis, and a pharmaceutically acceptable carrier.

15. The vaccine of embodiment 13 or 14, wherein the reovirus-induced viral arthritis/tenosynovitis is a variant group 2/genotype 1-induced viral arthritis/tenosynovitis.

16. An effervescent tablet comprising an avian reovirus, composition, or vaccine of any one of embodiments 1 to 15.

17. A method for reducing susceptibility of a bird of the order Galliformes against reovirus-induced viral arthritis/tenosynovitis, the method comprising administering to the bird an avian reovirus, composition, or vaccine of any one of embodiments 1 to 16.

18. A method for protecting a bird of the order Galliformes against reovirus-induced viral arthritis/tenosynovitis, the method comprising administering to the bird an avian reovirus, composition, or vaccine of any one of embodiments 1 to 16.

19. The method of embodiment 17 or 18, wherein the reovirus-induced viral arthritis/tenosynovitis is a variant group 1/genotype 5-induced viral arthritis/tenosynovitis.

20. The method of embodiment 17 or 18, wherein the reovirus-induced viral arthritis/tenosynovitis is a variant group 2/genotype 1-induced viral arthritis/tenosynovitis.

21. The method of any one of embodiments 17 to 20, wherein administration is intranasal, intraocular, oral, mucosal, intramuscular, or subcutaneous.

22. The method of any one of embodiments 17 to 20, wherein administration comprises in ovo administration.

23. The method of any one of embodiments 17 to 20, wherein the avian reovirus, composition, or vaccine is administered by aerosol.

24. The method of any one of embodiments 17 to 20, wherein the avian reovirus, composition, or vaccine is administered by drinking water.

25. The method of any one of embodiments 17 to 24, wherein administration comprises administration to a breeder hen or a rooster.

26. A method of producing anti-reovirus antibodies in poultry, the method comprising administering an isolated avian reovirus, composition, or vaccine of any one of embodiments 1 to 16 to the bird.

27. The method of any one of embodiments 17 to 26, wherein the bird is a chicken or turkey.

28. A diagnostic kit comprising an isolated avian reovirus of any one of embodiments 1 to 4.

29. A method of detecting exposure to an avian reovirus in a bird, the method comprising determining that an antisera sample obtained from the bird specifically binds to an avian reovirus of any one of embodiments 1 to 3.

30. A hyperimmune sera to an avian reovirus of ay one of embodiments 1 to 3.

31. An antibody that binds to an avian reovirus of any one of embodiments 1 to 3 and does not bind to avian reovirus strain S1133, 1733, 2408, and/or 2177.

32. The antibody of embodiment 31, wherein the antibody is a monoclonal antibody.

The present invention is illustrated by the following examples. It is to be understood that the particular examples, materials, amounts, and procedures are to be interpreted broadly in accordance with the scope and spirit of the invention as set forth herein.

EXAMPLES

Example 1

94826 C140—Variant Group 1/Genotype 5 Avian Reovirus

The attenuated avian reovirus 94826 C140 was obtained by passaging the 94826 avian reovirus 140 times in chicken embryos. Attenuated avian reovirus 94826 C140 was deposited with the ATCC® under Patent Deposit Designation as PTA-126077 on Aug. 13, 2019. Attenuated avian reovirus 94826 C140 is also archived as PDRC ref: 121116 in the virus repository at the Poultry Diagnostic and Research Center (PDRC) at the University of Georgia, located at 953 College Station Road Athens Georgia, 20602. The safety and efficacy of 94826 C140 as a live, attenuated reovirus vaccine is described in more detail in Example 3.

The parental 94826 avian reovirus is a Group 1/Genotype 5 avian reovirus and is described in more detail International Application No. PCT/US2015/013449 (WO 2015/116778) and U.S. patent application Ser. No. 15/223,623, both of which are incorporated herein by reference.

Example 2

96139 C140—Variant Group 2/Genotype 1 Avian Reovirus

The attenuated avian reovirus 96139 C140 was obtained by passaging the 96139 avian reovirus 140 times in chicken embryos. Attenuated avian reovirus 96139 C140 was deposited with the ATCC® under Patent Deposit Designation as PTA-126078 on Aug. 13, 2019. Attenuated avian reovirus 9619 C140 is also archived as PDRC ref: 119812 in the virus repository at the Poultry Diagnostic and Research Center (PDRC) at the University of Georgia, located at 953 College Station Road Athens Georgia, 20602. The safety and efficacy of 96139 C140 as a live, attenuated reovirus vaccine is described in more detail in Example 3.

The parental 96139 avian reovirus is Group 2/Genotype 1 avian reovirus, is described in more detail International Application No. PCT/US2015/013449 (WO 2015/116778) and U.S. patent application Ser. No. 15/223,623, both of which are incorporated herein by reference and was deposited with the ATCC® under Patent Deposit Designation as PTA-125688 on Mar. 7, 2019.

Example 3

Live Attenuated Reovirus Vaccine Candidates 94826 C140 and 96139 C140 Isolates The 94826 C140 avian reovirus, a variant Group 1/Genotype 5 avian reovirus, is as described in Example 1.

The 96139 C140 avian reovirus, a variant Group 2/Genotype 1 avian reovirus, is as described in Example 2. 96139 C140

Embryo Passages

Both virus isolates were passaged successively in specific pathogen free (SPF) embryos via the chorioallantoic membrane (CAM) route of inoculation. Specifically, CAM from the original isolate was diluted 1:100 in sterile Minimal essential media (MEM) and 0.1 ml inoculated into the CAM of 9-11 day old SPF embryos. At 48 hours post-inoculation, embryos were refrigerated at 4 C for 4 hours and CAMs from embryos were collected, pooled, homogenized in virus transport media (VTM) using the Omni bead ruptor, clarified at 1500×g and stored at −80 until the next embryo passage.

C140 Stock Titers

Stock titers for both 94826 C140 and 96139 C140 are shown in Table 1 below.

TABLE 1

| C140 stock titers represented as embryo infectious dose 50 per ml | |
|---|---|
| Virus | Titer (EID50/ml) |
| 94826 C140 | $10^{7.6}$ |
| 96139 C140 | $10^{8.2}$ |

Identity Testing

Identity testing was performed every 10-20 embryo passages. Briefly, aliquots of CAM passages were submitted for reovirus Sigma CRT-PCR, sequenced and nucleotide and amino acid sequences compared to original and previous passages to confirm identity.

Purity Testing

Purity testing was performed on the C140 stocks per guidelines set forth in 9 Code of Federal Regulations (9CFR) section 113.332 (9 CFR § 113.332), as well as, by culture and RT-PCR/PCR methods.

Bacteria, fungi, and mold culture indicated that both the 94826 C140 and 96139 C140 stocks were negative for bacteria, fungus, and mold by culture.

PCR indicated that both 94826 C140 and 96139 C140 stocks were negative for *Mycoplasma gallisepticum* (MG) and *Mycoplasma synoviae* (MS).

PCR/RT-PCR for extraneous viruses indicated that both the 94826 C140 and 96139 C140 stocks were negative for extraneous avian viruses.

The results for lymphoid leukosis contamination testing of stock viruses per guidelines set forth in 9 CFR § 113.332 (b)(2)(3) is shown in Table 2, below and indicated that both the 94826 C140 and 96139 C140 stocks are free of leukosis contamination.

TABLE 2

| Results of lymphoid leukosis contamination testing | | | | |
|---|---|---|---|---|
| Group | # birds$^A$ | Plasma tested by VI/LLAG$^B$ | REO ELISA (IDEXX) | AGP with stock reovirus |
| 94826 C140 @10$^{4.5}$ EID50 IM$^C$ | 10 | NEG | 3801 | POS |
| 96139 C140 @ 10$^{4.5}$ EID50IM | 10 | NEG | 3521 | POS |
| ALV-A Positive control | 5 | POS | NT | NT |
| ALV-B Positive control | 5 | POS | NT | NT |
| Negative controls | 5 | NEG | NEG | NEG |

$^A$3-week-old SPF birds
$^B$Virus Isolation in DF-1 cells and LLAG ELISA; tested in duplicate
$^C$Intramuscular Injection in breast muscle Safety Testing The CAM passages 140 (C140) for both isolates were safety tested per the guidelines outlined in the 9 Code of Federal Regulations (9CFR) section 113.332.

Experimental Outline

Bird source

Parent stock (broiler type birds) from Aviagen

Breeders vaccinated with commercial live and inactivated S1133

Broiler chicks negative for reovirus 94826 and 96139 antibodies

Safety test per 9 CFR

Parameters for evaluation per 9 CFR

94826 C140 (VG1/GT5) 10$^4$ EID50/0.2 ml [29 chicks]

94826 C140 (VG1/GT5) 10$^5$ EID50/0.2 ml [30 chicks]

96139 C140 (VG2/GT1) 10$^4$ EID50/0.2 ml [30 chicks]

96139 C140 (VG2/GT1) 10$^5$ EID50/0.2 ml [30 chicks]

Monitored daily for 21 days

Evaluation for lameness, tendon/hock swelling

Mortality

Results of the 10× evaluation in 1-day-old commercial broilers negative for antibodies to 94826 and 96139 are shown in Table 3, below. Results showed that no clinical signs or macroscopic lesions were observed in broilers subcutaneously injected 10$^4$ EID50 or 10$^5$ EID50 dose of 94826 or 96139 during the 21 day post-vaccination period of evaluation. Vaccines are considered safe for use in 1-day-old broilers at these doses.

TABLE 3

| Results of 10X safety study in 1-day-old broilers | | |
|---|---|---|
| Vaccine dose | Daily observations Clinical signs | 21 days-of-age Post-mortem examination |
| 94826 C140 (VG1/GT5) IQ$^4$ EID50/0.2 ml | No clinical signs observed in 29/29 birds | No macroscopic lesions observed in 29/29 birds |
| 94826 C140 (VG1/GT5) 10$^5$ EID50/0.2 ml | No clinical signs observed in 30/30 birds | No macroscopic lesions observed in 30/30 birds |
| 96139 C140 (VG2/GT1) IQ$^4$ EID50/0.2 ml | No clinical signs observed in 30/30 birds | No macroscopic lesions observed in 30/30 birds |
| 96139 C140 (VG2/GT1) 10$^5$ EID50/0.2 ml | No clinical signs observed in 30/30 birds | No macroscopic lesions observed in 30/30 birds |

Results of the 10× evaluation in 28-day-of age commercial broilers negative for antibodies to 94826 and 96139 are shown in Table 4, below. Results showed no clinical signs or macroscopic lesions were observed in broilers subcutaneously injected $10^4$ EID50 or $10^5$ EID50 dose of 94826 or 96139 during the 21 day post-vaccination period of evaluation. Vaccines are considered safe for use in 28-day-of-age broilers at these doses.

TABLE 4

| | Results of 10X safety study in 28-day-of-age broilers | |
|---|---|---|
| Vaccine dose | Daily observations Clinical signs | 21 days-of-age Post-mortem examination |
| 94826 C140 (VG1/GT5) $IQ^4$ EID50/0.2 ml | No clinical signs observed in 30/30 birds | No macroscopic lesions observed in 30/30 birds |
| 94826 C140 (VG1/GT5) $10^5$ EID50/0.2 ml | No clinical signs observed in 29/29 birds | No macroscopic lesions observed in 29/29 birds |
| 96139 C140 (VG2/GT1) $10^4$ EID50/0.2 ml | No clinical signs observed in 30/30 birds | No macroscopic lesions observed in 30/30 birds |
| 96139 C140 (VG2/GT1) $10^5$ EID50/0.2 ml | No clinical signs observed in 30/30 birds | No macroscopic lesions observed in 30/30 birds |

Efficacy Testing

The C140 stocks were evaluated for efficacy per 9 CFR 113.332 (4)(c)(1,2,3) Efficacy testing in 1-day-of-age broilers negative for reovirus antibodies to 94826 and 96139

Vaccinated/Subcutaneous injection

94826 C140 (VG1/GT5) $10^{2.5}$ EID50/0.2 ml [31 chicks]

94826 C140 (VG1/GT5) $10^3$ EID50/0.2 ml [31 chicks]

96139 C140 (VG2/GT1) $10^{2.5}$ EID50/0.2 ml [30 chicks]

96139 C140 (VG2/GT1) $10^3$ EID50/0.2 ml [30 chicks]

Unvaccinated Controls 20 chicks placed in isolation units at 1-day-of-age for unvaccinated/challenged controls 21-days-of-age (vaccinated/subQ and unvaccinated)

All groups challenged via footpad injection with $10^4$ EID50/0.05 ml 94826 Li7 or 96139 Li5 (parent viruses)

Observed daily for 14 days

Mortality

Depression

Lameness/limping

Swollen footpads and/or tendons

Results from efficacy testing in 1-day-of-age broilers are shown in Table 5, below. Results showed that 1-day-of-age chicks vaccinated with $10^{2.5}$ or $10^3$ EID50 per dose were protected following challenge with homologous parent viruses.

TABLE 5

| | Results from efficacy testing in 1-day-of-age broilers | | |
|---|---|---|---|
| Group Vaccinated at 1 doa[A] | Footpad Challenge 21 doa-$10^4$ EID[B] 50/dose | # birds | Clinical signs at 6 dpc[C] |
| 94826 C140 $10^{2.5}$ EID50/dose | 94826 Li7 | 31 | 31/31 NCS[D] |
| 94826 C140 $10^{3.0}$ EID50/dose | 94826 Li7 | 30 | 30/30 NCS |
| 96139 C140 $10^{2.5}$ EID50/dose | 96139 Li5 | 31 | 31/31 NCS |
| 96139 C140 $10^{3.0}$ EID50/dose | 96139 Li5 | 30 | 30/30 NCS |

[A]days-of-age

[B]embryo infectious dose

[C]days post challenge

[D]no clinical signs

Results from unvaccinated/parent virus challenged broilers are shown in Table 6, below. Results indicated that the efficacy test was valid based clinical signs observed in unvaccinated/challenged broilers.

TABLE 6

Results from unvaccinated/parent virus challenged broilers

| Group | Footpad Challenge at 21 days of age with $10^4$ EID$^A$ 50/dose | # birds | Clinical signs at 6 dpc$^B$ |
|---|---|---|---|
| Unvaccinated | 94826 Li7 | 10 | 10/10 redness/swelling |
| Unvaccinated | 96139 Li5 | 10 | 9/10 redness/swelling |

Results from the back titration of C140 stocks for 1-day-of age efficacy study-aliquots of diluted C140 stocks ($10^{2.5}$ and $10^3$ EID50/dose) titrated in embryos (5 replicates) are shown in Table 7, below.

TABLE 7

Titration of C140 reoviruses used in 1-day-of-age efficacy study.

| Virus | Titer EID50/dose | | | | | |
|---|---|---|---|---|---|---|
| | REP 1 | REP 2 | REP 3 | REP 4 | REP 5 | GMT |
| 94826 C140 $10^{2.5}$ EID50/dose | $10^{2.7}$ | $10^{2.1}$ | $10^{2.1}$ | $10^{2.5}$ | $10^{2.5}$ | $10^{2.4}$ |
| 94826 C140 $10^3$ EID50/dose | $10^{3.0}$ | $10^{3.1}$ | $10^{2.9}$ | $10^{3.0}$ | $10^{2.9}$ | $10^{3.0}$ |
| 96139 C140 $10^{2.5}$ EID50/dose | $10^{2.9}$ | $10^{2.5}$ | $10^{2.5}$ | $10^{2.5}$ | $10^{2.6}$ | $10^{2.6}$ |
| 96139 C140 $10^3$ EID50/dose | $10^{2.9}$ | $10^{2.9}$ | $10^{3.1}$ | $10^{3.1}$ | $10^{3.1}$ | $10^{3.0}$ |

GMT = geometric mean titer

Summary of Efficacy Testing in 1-Day-of-Age Broilers

Day-of-age vaccination with 94826 C140 or 96139 C140 at $10^{25}$ and $10^3$ doses protected against clinical signs following footpad challenge with parent viruses.

Unvaccinated/challenged controls fell within acceptable limits outlined in outlined in 9CFR 113.332 (4)(c)(3) for both parent viruses.

Testing in 1-day-old broilers was acceptable per 9CFR guidelines.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated avian reovirus, wherein the isolated avian reovirus is the avian reovirus strain 94826 C140 deposited at the ATCC under Patent Designation PTA-126077.

2. The isolated avian reovirus of claim 1, wherein the isolated avian reovirus is lyophilized, freeze dried, frozen, or an effervescent tablet.

3. A composition comprising the isolated avian reovirus of claim 1.

4. The composition of claim 3, wherein the composition is formulated:

for intranasal, intraocular, oral, mucosal, intramuscular, subcutaneous, or in ovo administration; or for spraying or aerolizing.

5. The composition of claim 3 comprising an adjuvant.

6. A vaccine comprising the isolated avian reovirus of claim 1.

7. The vaccine of claim 6, wherein the vaccine reduces the susceptibility of a bird of the order Galliformes to reovirus-induced viral arthritis/tenosynovitis.

8. A method for reducing susceptibility of a bird of the order Galliformes against reovirus-induced viral arthritis/tenosynovitis, the method comprising administering to the bird an avian reovirus of claim 1.

9. The method of claim 8, wherein administration comprises:

intranasal, intraocular, oral, mucosal, intramuscular, or subcutaneous administration;

in ovo administration;

administration by aerosol; or administration by drinking water.

10. The method of claim 8, wherein administration comprises administration to a breeder hen or a rooster.

11. The method of claim 8, wherein the bird is a chicken or turkey.

12. A method for protecting a bird of the order Galliformes against reovirus-induced viral arthritis/tenosynovitis, the method comprising administering to the bird an avian reovirus of claim 1.

13. A diagnostic kit comprising an isolated avian reovirus of claim 1.

14. An isolated avian reovirus, wherein the isolated avian reovirus is the avian reovirus strain 96139 C140 deposited at the ATCC under Patent Designation PTA-126078.

15. The isolated avian reovirus of claim 14, wherein the isolated avian reovirus is lyophilized, freeze dried, frozen, or an effervescent tablet.

16. A composition comprising the isolated avian reovirus of claim 14.

17. The composition of claim 16 comprising an adjuvant.

18. The composition of claim 16, wherein the composition is formulated:

for intranasal, intraocular, oral, mucosal, intramuscular, subcutaneous, or in ovo administration; or for spraying or aerolizing.

19. A vaccine comprising the isolated avian reovirus of claim 14.

20. The vaccine of claim 19, wherein the vaccine reduces the susceptibility of a bird of the order Galliformes to reovirus-induced viral arthritis/tenosynovitis.

21. A method for reducing susceptibility of a bird of the order Galliformes against reovirus-induced viral arthritis/tenosynovitis, the method comprising administering to the bird an avian reovirus of claim 14.

22. The method of claim 21, wherein administration comprises:

intranasal, intraocular, oral, mucosal, intramuscular, or subcutaneous administration;

in ovo administration;

administration by aerosol; or administration by drinking water.

23. The method of claim 21, wherein administration comprises administration to a breeder hen or a rooster.

24. The method of claim 21, wherein the bird is a chicken or turkey.

25. A diagnostic kit comprising an isolated avian reovirus of claim 14.

26. A method for protecting a bird of the order Galliformes against reovirus-induced viral arthritis/tenosynovitis, the method comprising administering to the bird an avian reovirus of claim 14.

\* \* \* \* \*